United States Patent
Scantlebury et al.

(10) Patent No.: US 7,863,499 B2
(45) Date of Patent: Jan. 4, 2011

(54) MODEL OF INFANTILE SPASM SYNDROME

(75) Inventors: Morris H. Scantlebury, Bronx, NY (US); Solomon L. Moshe, Chappaqua, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 309 days.

(21) Appl. No.: 12/009,927

(22) Filed: Jan. 23, 2008

(65) Prior Publication Data

US 2008/0216183 A1    Sep. 4, 2008

Related U.S. Application Data

(60) Provisional application No. 60/900,487, filed on Feb. 8, 2007.

(51) Int. Cl.
*A01K 67/00* (2006.01)
*A61K 49/00* (2006.01)

(52) U.S. Cl. .................. 800/9; 800/8; 424/9.2

(58) Field of Classification Search ........... 800/9, 800/8; 424/9.2
See application file for complete search history.

(56) References Cited

PUBLICATIONS

Siegal et al. (1988), J. Neuro-Oncol., vol. 6, 135-140.*
Stafstrom et al. (2006) Epilepsia, vol. 47 (8), 1407-1414.*
Stafstrom and Holmes (2002) Int. Rev. Neurobiol., vol. 49, 391-410.*
Lee CL et al. A new animal model of infantile spasms wth unprovoked persistent seizures. Epilepsia, 2007, Oct. 18, pp. 1-10 [Epub].
Pang Y et al., entitled "Disturbance of oligodendrocyte development, hypomyelination and white matter injury in the neonatal rat brain after intracerebral injection of lipopolysaccharide," Developmental Brain Research, 14, 2003, pp. 205-214.
Pflieger J F et al., entitled "Postural Modifications and Neuronal Excitability Changes Induced by a Short-Term Serotonin Depletion during Neonatal Development in the Rat," The Journal of Neuroscience, Jun. 15, 2002, 22(12), pp. 5108-5117.
Scantlebury MH et al. A New Animal of Infantile Spasms. American Epilepsy Society Abstract, 2006, 2 pages.
Siegal T et al., entitled "Early and delayed neurotoxicity of Mitoxantrone and Doxorubicin following subarachnoid injection," Journal of Neuro-Oncology 6, 1988, pp. 135-140.
Stafstrom C E et al., entitled "Infantile Spasms: Criteria for an Animal Model," International Review of Neurobiology, 2002, vol. 49, pp. 391-410.
Stafstrom C E et al., entitled "Models of pediatric epilepsies: strategies and opportunities," Epilepsia, 2006, Aug. 47, 8, pp. 1407-1414.
Velisek L et al., entitled "Model of Infantile Spasms Induced by N-Methyl-D-Aspartic Acid in Prenatally Impaired Brain," Ann Neurol 2007, 61, pp. 109-119.

* cited by examiner

*Primary Examiner*—Anne Marie S Wehbe
(74) *Attorney, Agent, or Firm*—Amster, Rothstein & Ebenstein LLP

(57) ABSTRACT

Provided are non-human mammals treated with doxorubicin, lipopolysaccharide (LPS), and p-chlorophenylalanine (PCPA), where the mammal exhibits a symptom characteristic of infantile spasms. Also provided are methods of making a non-human mammal exhibit a symptom of infantile spasms. Additionally, methods are provided for screening a compound for the potential to attenuate a symptom of infantile spasms.

21 Claims, 10 Drawing Sheets

Scenario 1
- Increased cortical excitability (enhanced epileptogenicity).
- Inefficient brainstem modulation of cortex.

— White Matter —

Scenario 2
- Increased brainstem excitability (enhanced epileptogenicity).
- Abnormal cortical modulation of brainstem.

MODEL OF INFANTILE SPASM SYNDROME

CROSS-REFERENCE TO RELATED APPLICATION

This application claims the benefit of U.S. Provisional Application No. 60/900,487, filed on Feb. 8, 2007, the content of which is incorporated by reference.

FIELD OF THE INVENTION

The present invention generally relates to animal models of human diseases. More specifically, the invention is directed to an animal model of the infantile spasm syndrome.

BACKGROUND OF THE INVENTION

Throughout this application various publications are referred to in parenthesis. Citations for these references may be found at the end of the specification preceding the claims. The disclosures of these publications are hereby incorporated by reference in their entireties into the subject application to more fully describe the art to which the subject application pertains.

Infantile spasm syndrome, or infantile spasms (IS), represents an age-related epileptic syndrome characterized by brief spasms, specific EEG patterns [hypsarrhythmia (interictally) and electrodecremental responses (ictally)], with frequent subsequent cognitive deterioration. The incidence of IS is 2.5 per 10,000 live births (Bobo et al., 1994; Hrachovy and Frost, 2003) with a slight (60%) male predominance (Webb et al., 1996). The causes of IS are diverse and can be multifactorial, often a combination of genetic predisposition (Mizukawa et al., 1992; Bingham et al., 1996; Dulac et al., 1993a) and environmental insults (Watanabe, 1998). IS can be classified into symptomatic, cryptogenic and idiopathic groups (Id.). Symptomatic IS are considered the consequence of a known CNS disorder and comprise the largest proportion of cases (Hrachovy and Frost, 2003; Watanabe, 1998). IS can occur following multiple etiologies, including brain malformations such as tuberous sclerosis, hypoxic ischemic injury, trauma, toxins and infections, often as a combination of additive insults (Watanabe, 1998; Short et al., 1995; Saktik et al., 2003; Alvarez et al., 1987; Cusmai et al., 1993). The extent of abnormalities can be documented with MRI in vivo or in post mortem examination (Watanabe, 1998, Saltik et al., 2003; Hashimoto et al., 1990). In one recent review, over 200 etiological and associative factors were linked to IS (Hrachovy and Frost, 2003). In the cryptogenic group, a CNS abnormality is suspected but remains unidentified. In the idiopathic group, the cause is unknown and suspected to be genetic. In both idiopathic or cryptogenic IS, the MRI does not show any abnormalities (Watanabe, 1998). After the onset of IS, many patients may begin losing developmental milestones and, subsequently, may become mentally retarded, as the epileptic encephalopathy progresses (Kurokawa et al., 1980; Riikonen, 1982; Riikonen and Amnell, 1981; Koo et al., 1993; Favata et al., 1987). The prognosis is somewhat better in patients with cryptogenic or idiopathic IS (Lombroso, 1983; Pang et al., 2003; Dulac et al., 1993b). In the majority of the cases, IS have their onset between 3-7 months of age and 85% start before one year of age (Jeavons et al., 1973). IS commonly occur during transitions in the sleep wake cycle (Baird, 1959; Druckman and Chao, 1955; Kellaway et al., 1979; King et al., 1985), often in clusters (Kellaway et al., 1979; King et al., 1985; West, 1841; Plouin et al., 1993). They involve flexion of the neck and upper body and adduction of the arm (flexion spasms) (West, 1841) or contractions of the extensor muscles with sudden extension of the neck and trunk with extension and abduction of the limbs (extension spasms) (Caraballo et al., 2003). The ictal EEG pattern consists of an electrodecremental response (Kellaway et al., 1979; Plouin et al., 1993; Maheshwari and Jeavons, 1975). The interictal EEG recordings show a disorganized high voltage background with multifocal spikes called hypsarrhythmia (Gibbs and Gibbs, 1952). It has been suggested that early recognition of IS and institution of early treatment is required to improve outcome (Curatolo, 2005). Unfortunately, IS are not often controlled by conventional AEDs (Haines and Casto, 1994). The most widely accepted treatment is administration of ACTH (Snead et al., 1983; Baram et al., 1996; Mackay et al., 2004), a potentially toxic agent (Satoh et al., 1982). The response to treatment with ACTH is variable ranging from 40 to 100% (Mackay et al., 2004). ACTH is more effective in treating idiopathic/cryptogenic IS than symptomatic IS (Wolf and Moshe, 2002). When effective, ACTH leads to the cessation of spasms although after treatment is stopped, the spasms may recur (Snead et al., 1983; Baram et al., 1996; Mackay et al., 2004; Pollack et al., 1979). Vigabatrin (another potentially toxic agent) is effective in some cases too, especially in IS associated with tuberous sclerosis (Mackay et al., 2004; Lux et al., 2005; Vigevano and Cilio, 1997). Clinical studies show that IS may spontaneously remit between 12-24 months of age (Bachman, 1981; Hrachovy et al., 1991; Dulac et al., 1997). However, the cognitive deficits persist and the children are often mentally retarded (Caplan et al., 2002). Furthermore, new seizure types (including partial seizures without and with secondary generalization) may emerge often intractable to treatment with AEDs (Riikonen, 1982; Jeavons et al., 1973; Jeavons and Bower, 1961; Rantala and Putkonen, 1999). Finally, IS are associated with high mortality rates. Review of the literature suggests that 5-30% of the children with IS die. Of these deaths 50% are disease-related and 50% treatment-related (Riikonen, 1982; Snead et al., 1983; Rantala and Putkonen, 1999; Appleton, 2001; Mackay et al., 2002). Mortality is greater in symptomatic cases (Dulac et al., 1997).

Because IS are associated with dismal outcomes, it is important to develop innovative, effective, non-toxic treatments to promptly stop the seizures and the regression. This will require the identification of a model system to be used to identify new treatments and screen for efficacy in preclinical studies. A successful model would be expected to meet certain minimum criteria outlined at the "Models of Pediatric Epilepsies," workshop, held in Bethesda, Md. on May 13-14, 2004. The Workshop was sponsored by NIH/NINDS, in conjunction with the American Epilepsy Society and the International League Against Epilepsy and summarized in Stafstrom et al., 2006). The proposed minimum criteria include 1) spontaneous recurrent epileptic spasms that occur within a developmental window corresponding to that seen in humans; 2) the tonic spasms should be associated with cortical EEG electrodecremental discharges; 3) the epileptic spasms should be responsive to some degree to ACTH or vigabatrin treatment; and 4) evidence for behavioral and cognitive sequelae. In addition, another criterion was considered: the cortical interictal EEG should show hypsarrhythmia. Because the definition of hypsarrhythmia includes the presence of multifocal, high amplitude discharges (Gibbs and Gibbs, 1952), this pattern may be extremely difficult to realize in a rat or mouse pup where placement of multiple electrodes in the brain is limited by its size and fragility of skull bones. Therefore, modeling of hypsarrhythmia may be restricted to larger animal models until technological advances permit the development of "micro" electrode assemblies (Stafstrom et al., 2006).

Animal models of the human IS phenotype have been especially difficult to generate. In the NIH/NINDS workshop, the participants discussed various attempts to create such models. One model involves i.c.v. administration of picomolar amounts of corticotrophin releasing hormone (CRH) to neonatal rats (Brunson et al., 2001b), an interesting approach given the peculiar response of IS to ACTH. Further, the perinatal stress caused by etiologies associated with IS has led to the hypothesis that stress may increase endogenous CRH levels in seizure-prone areas of the developing brain, leading to neuronal damage, axonal reorganization and long-term cognitive deficits (Avishai-Eliner et al., 2002). However, the consensus was that, although CRH-treated rats display cognitive deficiencies, the CRH-induced seizure phenotype is (primarily "limbic") and the EEG abnormalities do not mimic features of IS. Moreover and the seizures are not responsive to ACTH; however ACTH does reduce CRH gene expression in certain neuronal populations (Brunson et al., 2001a). Another attempt to model IS involves one i.p. injection of NMDA in infant rats (Kabova et al., 1999; Stafstrom and Sasaki-Adams, 2003). This agent causes a clinical seizure described as 'emprosthotonus', consisting of whole-body tonic flexion with back-arching. These seizures are often accompanied by a diffuse attenuation of the EEG amplitude, but without any epileptiform discharges. Furthermore, spontaneous seizures have not been recorded and hormonal pretreatment (with hydrocortisone) does not decrease but instead increases the frequency of the 'emprosthotonic' seizures. However, if the pups are prenatally exposed to betamethasone, pretreatment with ACTH, prior to the administration of NMDA, increases the latency to the onset of the 'emprosthotonic' seizures. This observation together with the fact that there is no preexisting structural pathology has led to the hypothesis that this may be a model of idiopathic IS (Velisek et al. 2007). Lee et al have also recently reported that intracerebral infusions of tetrodotoxin in rat pups for several weeks starting on the 10th day of life lead to the development of spontaneous recurrent seizures in adulthood (Lee, Frost et al. 2006). The seizures are characterized by frequent head nodding or myclonic jerks involving the whole body; the ictal EEG often shows a slow wave followed by generalized voltage attenuation resembling an electrodecremental discharge. Some rats with seizures also have diffuse EEG multifocal discharges resembling hypsarrythmia. In this model, however, the seizures occur in adulthood. The observation of seizures in adult animals is not consistent with the human data where IS occur early in life.

SUMMARY OF THE INVENTION

The inventors have discovered methods of treating non-human mammals such that the animals develop symptoms similar to those seen in humans exhibiting infantile spasms. The invention is directed to methods and compositions related thereto.

The invention is directed to non-human mammals treated with doxorubicin, lipopolysaccharide (LPS), and p-chlorophenylalanine (PCPA). These invention mammals exhibit a symptom characteristic of infantile spasms.

The invention is also directed to methods of making a non-human mammal exhibit a symptom of infantile spasms. The methods comprise treating the non-human mammal with doxorubicin, lipopolysaccharide (LPS), and p-chlorophenylalanine (PCPA).

The invention is additionally directed to methods of screening a compound for the potential to attenuate a symptom of infantile spasms. The methods comprise administering the compound to the above-described mammal that has been treated with doxorubicin, lipopolysaccharide (LPS), and p-chlorophenylalanine (PCPA), and determining whether the compound attenuates a symptom characteristic of infantile spasms in the mammal.

DETAILED DESCRIPTION OF THE INVENTION

Figure 1:
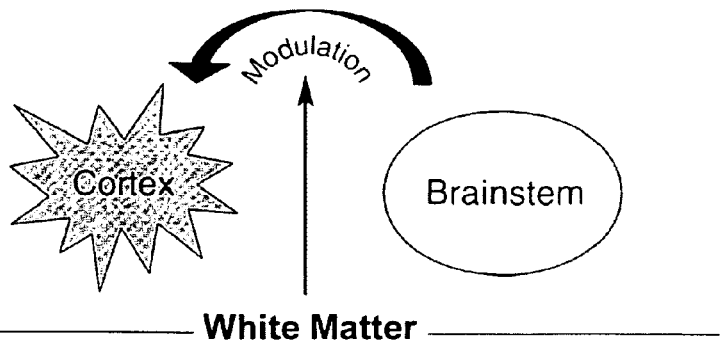
FIG. 1 is a schematic diagram outlining scenarios whereby changes in cortex or brain stem regions may result in IS and the putative role of white matter (from Lado and Moshe, 2002).
Figure 1:
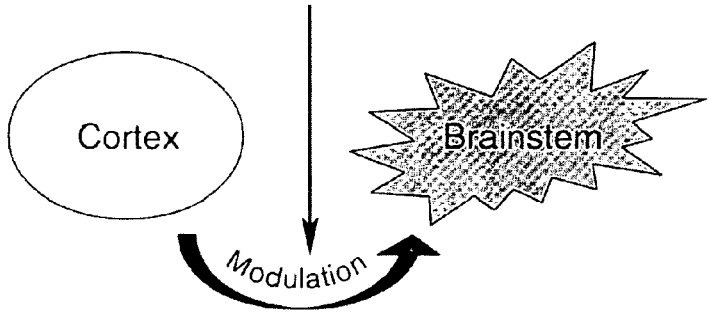

The inventors have discovered methods of treating non-human mammals such that the animals develop symptoms similar to those seen in humans exhibiting infantile spasms (IS). These animals are useful for developing medications and other therapies to treat IS. The invention is thus directed to methods and compositions related thereto.

The invention is directed to non-human mammals treated with doxorubicin, lipopolysaccharide (LPS), and p-chlorophenylalanine (PCPA). These invention mammals exhibit a symptom characteristic of infantile spasms. See Example. These three treatments can be administered in any manner that allows the compounds to enter the brain in order to contribute to the development of IS symptoms. Preferably, the doxorubicin is administered intracerebrally. It is also preferred that the LPS is administered intracerebrally. Also preferably, the PCPA is administered systemically. More preferably, the doxorubicin is administered intracerebrally, the LPS is administered intracerebrally, and the PCPA is administered systemically. The most preferred route of doxorubicin administration is injection intracerebroventricularly (i.c.v.). With this i.c.v. doxorubicin administration, the most preferred administration of LPS is intracerebrally, and the most preferred administration of the PCPA is systemically.

Any non-human mammal can be used for these animal models. Preferably, the mammal is a rodent. More preferably, the mammal is a rat.

Preferably, the treatments are made before day 10 after the birth of the mammal. When the mammal is a rat, the rat is preferably treated with the doxorubicin and LPS at day 2, 3 or 4 after birth and the PCPA at day 4, 5, or 6 after birth. Most preferably, the rat is treated with the doxorubicin and LPS at day 3 after birth and the PCPA at day 5 after birth. The mammals preferably do not undergo all three treatments on the same day, since the stress on the mammal under such a regimen would be excessive.

With any mammal, the mammal is preferably treated with the doxorubicin and LPS at an age that is developmentally equivalent to a rat at day 2, 3 or 4 after birth, and the mammal is treated with the PCPA at an age that is developmentally equivalent to a rat at day 4, 5 or 6 after birth. Most preferably, the mammal is treated with the doxorubicin and LPS at an age that is developmentally equivalent to a rat at day 3 after birth, and the mammal is treated with the PCPA at an age that is developmentally equivalent to a rat at day 5 after birth.

Preferably, 0.1-5 µg/g doxorubicin is injected, 0.1-5 µg/g LPS is injected, and 30-1000 mg/kg PCPA is injected. More preferably, 0.5-2 µg/g doxorubicin is injected, 0.5-2 µg/g LPS is injected, and 100-600 mg/kg PCPA is injected. Most preferably, about 1 µg/g doxorubicin is injected, about 1 µg/g LPS is injected, and about 300 mg/kg PCPA is injected.

With some of these mammals, the symptom characteristic of infantile spasms resolves by day 15 after birth. With others, the symptom does not resolve by day 15 after birth. In some cases, the symptom progresses to a spontaneous epileptic seizure after day 11.

The invention mammals can exhibit any symptom characteristic of infantile spasms. Often, the mammals exhibit several symptoms characteristic of infantile spasms. With some preferred mammals, the symptom is a spontaneous, recurrent seizure. The seizure could be a flexion spasm. The seizure could also be an extension spasm. Additionally, the mammal could exhibit both flexion spasms and extension spasms. The mammals exhibiting seizures preferably also exhibit rapid polyspike activity preceding the seizure on an ictal EEG.

Another useful symptom characteristic of infantile spasms that is present in the invention mammals is a deficiency in motor development. Preferred deficiencies in motor development are in surface righting, negative geotaxis, cliff aversion, open field activity, rooting, forelimb placing, air righting, eye-opening, horizontal bar, rotarod or a Morris water-maze test. Most preferably, the deficiency in motor development is in surface righting, negative geotaxis or open field activity.

The deficiency in motor development can be evaluated by any test known in the art. Preferred examples of developmental tests are as follows (see, e.g., Mikulecka and Mares, 2002; Poggi et al., 2005; Khan et al., 2006):

1. Surface righting: The time taken for the mammal pup placed supine to return to the prone position with all 4 paws on the ground. Pups are preferably tested for 60 seconds.
2. Negative geotaxis: The time taken for pups placed head down at a 45° incline to turn 90° and begin to crawl back up the slope. Pups are preferably tested for 30 seconds.
3. Cliff Aversion: The time taken for pups positioned with forepaws and snout over the edge of a shelf to turn and begin to crawl away from the edge. Pups are preferably tested for 60 seconds.
4. Open field activity: Time taken for pups to exit a 13 cm circle in diameter after being placed in the center. Pups are preferably tested for 60 seconds.
5. Rooting: Head turn towards the side of the face being stroked.
6. Forelimb placing: Grasps a dowel being stroked against the dorsal surface of the paw.
7. Air righting: Pups are released upside down form a height of 60 cm turn right-side up and land on all four paws on a bed of shavings.
8. Eye opening: The day of opening of the eyes is noted.
9. Horizontal bar: Pups are preferably placed on a 25 cm long wooden bar (2 cm in diameter) extended between two poles 50 cm high. Pups then grasp the bar with their fore and hind limbs. The time spent on the bar is preferably recorded for up to 120 seconds.
10. Rotarod: Pups are preferably placed on a rotating rod that is 10 cm in diameter (speed 5 rpm). The time spent on the rod is preferably measured up to 180 seconds.
11. Morris water maze: Pups are placed in a circular pool filled with opaque water to find the location of a hidden platform. Where the mammal is a rat, pups are preferably first trained on day 1-6 and tested on day 7. On day 7, the platform is removed and a probe trial is performed to assess the spatial bias in the rats' search patterns. The time taken to reach the previous location of the platform is assessed. The swim patterns are preferably videotaped for later review and analysis.

After the spasms disappear a new seizure type (limbic) may emerge. The seizures can be measured and scored by any means known. A preferred example of scoring seizures is described in Veliskova, 2006, as follows. Seizure stage 0: Behavioral arrest; 1: Mouth clonus; 2: Head bobbing; 3: Unilateral forelimb clonus; 3.5: Alternating forelimb clonus; 4: Bilateral forelimb clonus; 5: Bilateral forelimb clonus with rearing and falling; 6: Wild running and jumping with vocalization; 7: Tonus The invention is also directed to methods of making a non-human mammal exhibit a symptom of infantile spasms. The methods comprise treating the non-human mammal with doxorubicin, lipopolysaccharide (LPS), and p-chlorophenylalanine (PCPA). The invention mammals described above are created by these methods.

Preferably, the doxorubicin is administered intracerebrally, the LPS is administered intracerebrally, and the PCPA is administered systemically. The mammal is preferably a rodent, most preferably a rat.

In these methods, a symptom that the non-human mammal preferably exhibits is a spontaneous, recurrent seizure. The seizure is preferably a flexion spasm. Another preferred seizure type is an extension spasm. Most preferably, the mammal exhibits rapid polyspike activity preceding the seizure on an ictal EEG.

Another preferred symptom of infantile spasms elicited by these methods is a deficiency in motor development.

The mammals discussed above are useful for evaluating treatments for infantile spasms. The proposed treatment is administered to the mammal and the mammal is evaluated to determine the effect of the treatment on the IS symptom being evaluated by the investigator. Thus, the invention is additionally directed to methods of screening a compound for the potential to attenuate a symptom of infantile spasms. The methods comprise administering the compound to the above-described the mammal that has been treated with doxorubicin, lipopolysaccharide (LPS), and p-chlorophenylalanine (PCPA), and determining whether the compound attenuates a symptom characteristic of infantile spasms in the mammal.

In these methods, the mammal is preferably a rat treated with the doxorubicin and LPS at day 2-4 after birth and the PCPA at day 4-6 after birth. A preferred symptom evaluated in these methods is a spontaneous, recurrent seizure. More preferably, the seizure is accompanied by rapid polyspike activity preceding the seizure on an ictal EEG. Another preferred symptom evaluated in these methods is a deficiency in motor development.

It is believed that these methods could also reveal a treatment for a seizure disease that is not IS. Thus, in some preferred aspects of these methods, the compound can attenuate a symptom of a seizure disease that is not infantile spasms.

Preferred embodiments of the invention are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXPERIMENTAL DETAILS

Example 1

Development of an Animal Model for Infantile Spasms

Evidence is provided suggesting the creation of a new model of symptomatic IS in infant rats. The model fulfills at least two of the criteria suggested by the workshop: recurrent spasms over several days associated with ictal seizure discharges resembling in part the EEG features seen in humans including electrodecremental-like responses. Furthermore, similar to the clinical situation, the spasms persist for a specific period of time from P7 to P11-12. As the spasms disappear, several pups go on to develop other spontaneous seizures manifesting as behavioral arrest and secondarily generalized limbic seizures (Racine et al., 1973; McNamara, 1984; Bertram and Cornett, 1993; Haas et al., 1990).

In creating the model, the necessary substrates for the expression of IS were evaluated. There are several hypotheses based on anatomical, functional and biochemical abnormalities that are sometimes observed in patients with IS. There is evidence that both cortical and subcortical structures may have an important role. For example, surgical series indicate that in some highly selective patients with tuberous sclerosis, removal of the offending cortical lesion may lead to complete cessation of the spasms, implying a cortically-based pathology (Kagawa et al., 2005; Asano et al., 2005). Another model proposes that the existence of a cortical epileptic abnormality which can excite the brainstem and/or striatum resulting in spasms (Chugani et al., 1992; Rho, 2004). The usually bilateral synchronous phenotypic expression of the spasms suggests subcortical involvement (Lado and Moshe, 2002). There is also evidence that IS can occur in patients with predominantly brainstem abnormalities (Morimatsu et al., 1972; Satoh et al., 1986; Hayashi et al., 2000). Behaviorally, the spasms are considered to be tonic seizures and tonic seizures are thought to arise from the brainstem (Bernham, 1985). Spasms tend to cluster around the sleep/wake transition (Baird, 1959; Druckman and Chao, 1955; Kellaway et al., 1979; King et al., 1985), which suggests a role for the brainstem pontine reticular formation Hobson et al., 1974). Abnormalities in brainstem serotonin metabolism have been proposed as an underlying pathophysiologic mechanism for IS (Juhasz et al., 2002). In some patients with IS low CSF levels of the serotonin metabolite, 5-hydroxyindoleacetic acid (5HIAA) have been observed (Silverstein and Johnson, 1984). It has been proposed that the low levels of CSF serotonin in patients with IS may be the result of abnormal metabolism of tryptophan (Yamamoto et al., 1995). Tryptophan is an amino acid that is normally hydroxylated and converted to serotonin. Failure of this pathway will result in tryptophan being metabolized alternatively through the kynurenine pathway. This would result in an increased production of quinolinic acid, which can lead to hyperexcitability and seizures (Schwarcz et al., 1986).

Along with neuronal damage to the cortex and brainstem, white matter injury may play a role in the expression of seizures in IS (Watanabe, 1998; Okumura et al., 1996; Higuchi et al., 1997; Caraballo et al., 1997). Delayed myelination is also a frequent finding (Saltik et al., 2003; Kasai et al., 1995; Natsume et al., 1996; Watanabe et al., 1994). In a recent review, Lado and Moshé (2002) hypothesized that structural or functional abnormalities that lead to hyperexcitability in either or both the cortex and brainstem, along with abnormal communication between these two regions (such as may result with white matter injury), may be necessary to produce IS (FIG. 1). The following method was used to induce, within a short period of time, injury to the cortex, brainstem and white matter in rat pups. At P3 injected doxorubicin (DOX) was injected i.c.v. and lipopolysaccharide (LPS) intracerebrally in the right centroparietal cortex and at P5, p-chlorophenylalanine (PCPA) was injected i.p. DOX is an antineoplastic agent that, when injected into adult rats, results in diffuse damage involving forebrain and brainstem (Siegal et al., 1988); there are no published data regarding its effects in pups. Intracerebral injections of LPS in P5 rat pups results in hypomyelination including white matter rarefaction and necrosis (Pang et al., 2003). PCPA depletes serotonin by inhibiting the enzyme tryptophan hydroxylase, which catalyzes the conversion of tryptophan to serotonin (Rattray et al., 1996). Inhibition of tryptophan hydroxylase may also lead to an increased production of quinolinic acid (Schwarcz et al., 1986).

Pups injected with DOX, LPS and PCPA develop agespecific, spontaneous, recurrent seizures that resemble the epileptic spasms in human infants; the spasms are associated with ictal electrographic discharges reminiscent of the ictal discharges observed in humans. Furthermore, some pups develop limbic seizures upon cessation of the spasms. Experimental pups also show marked deficits in behavioral testing. This is partly due to the injury induced by the injections of DOX, LPS and PCPA; however the deficits appear to be more pronounced after spasms emerge. Histological analysis revealed diffuse damage to cortical and subcortical structures and white matter, consistent with the hypothesis that damage to these structures may be necessary for the development of some forms of symptomatic IS.

Experimental

The combination of LPS, DOX and PCPA was administered to pups of both sexes. The pups were injected with DOX i.c.v. and LPS intracerebrally in the right centroparietal cortex at P3; PCPA was administered i.p. at P5. Two additional pups were injected with PCPA alone. There were no sex differences and the data were combined.

Figure 2:
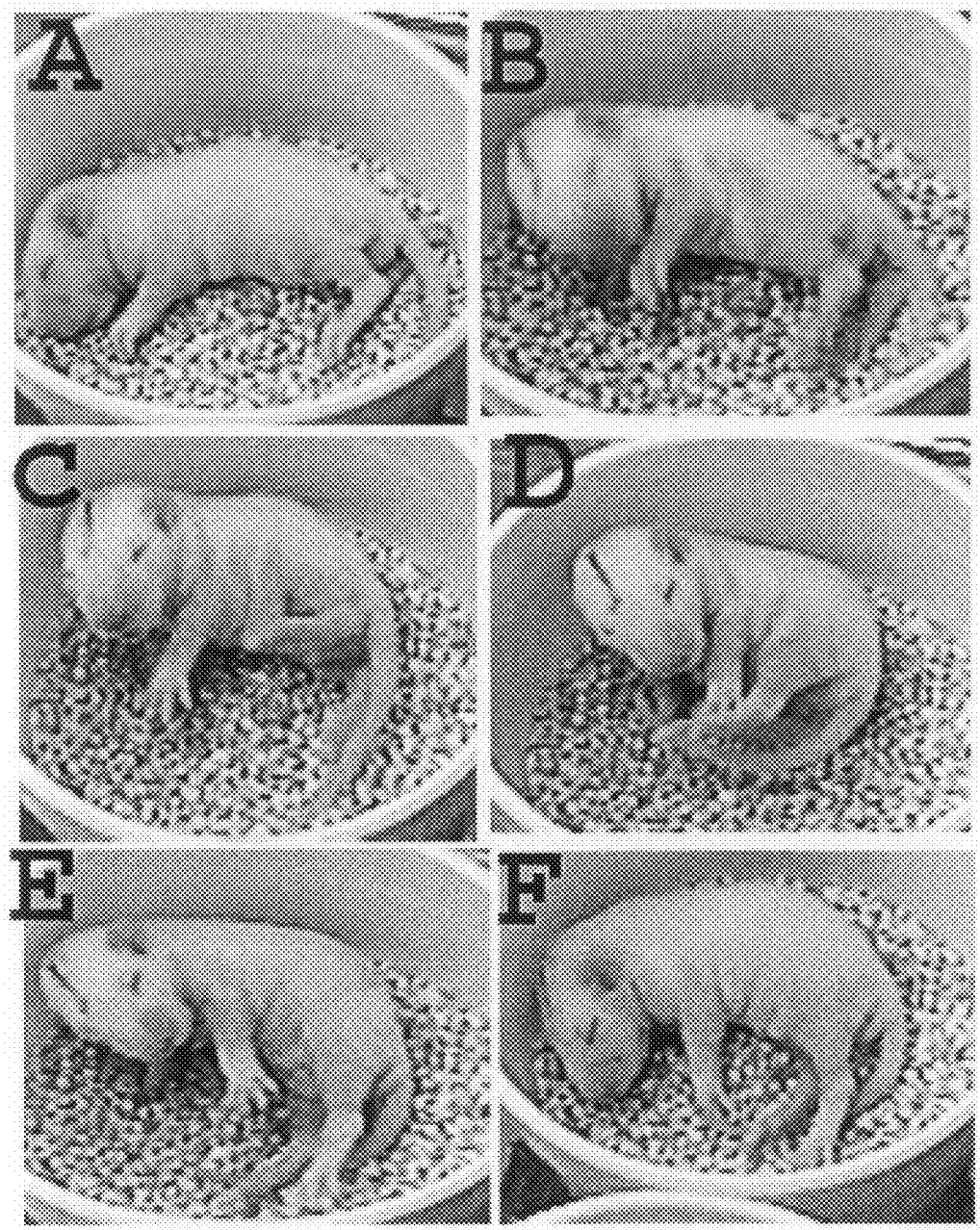
FIG. 2A-2F is photographs of rat pups treated according to the invention showing flexion spasm in a P9 rat following injections of DOX and LPS at P3 and PCPA at P5. In Panel A, the pup is lying on its side prior to the spasm. In Panel B, the pup raises its head abruptly at the start of the spasm. This is followed by flexion of the trunk, extension of the left forelimb and flexion of the left hindlimb (Panel C). The head is still raised. In Panel D, the trunk is maximally flexed and there is extension of the left forelimb and both hindlimbs (Panel E). The end of the spasm starts with relaxation of the trunk, however there is continued extension and abduction of the left forelimb. The left hindlimb is still mildly extended. Panel F shows the post-ictal state. The pup is resting in a mildly flexed position prior to the emergence of a second spasm.

Behavioral seizures and spasm-like episodes. Ten rat pups were videotaped daily for 45 minutes per day from P5 till P12. Seven pups had recurrent seizures resembling spasms. Spasms were first observed at P7 in 60% of the pups. At P9, spasms were observed in 70% of the pups. The spasms were characterized by the abrupt onset of flexion of the trunk with extension of the limbs at the height of the spasm (the sequence is shown in FIG. 2). In two pups, extension spasms were sometimes observed. The spasms lasted from 1 to 5 seconds. Spasms were not observed in pups at P12.

Spasms are associated with ictal EEG activity. EEGs were recorded from the left hippocampus in three additional pups injected with DOX, LPS and PCPA that developed flexion spasms and in one non-injected control. The electrodes were inserted at P9 into the hemisphere contralateral to the injections of DOX and LPS. The EEG recordings were obtained during a 45 min session once in two experimental pups and in three consecutive days in the other experimental pup and control pup. The naïve control pup did not have spasms or focal seizures and the EEG did not contain any epileptiform discharges.

Figure 3:
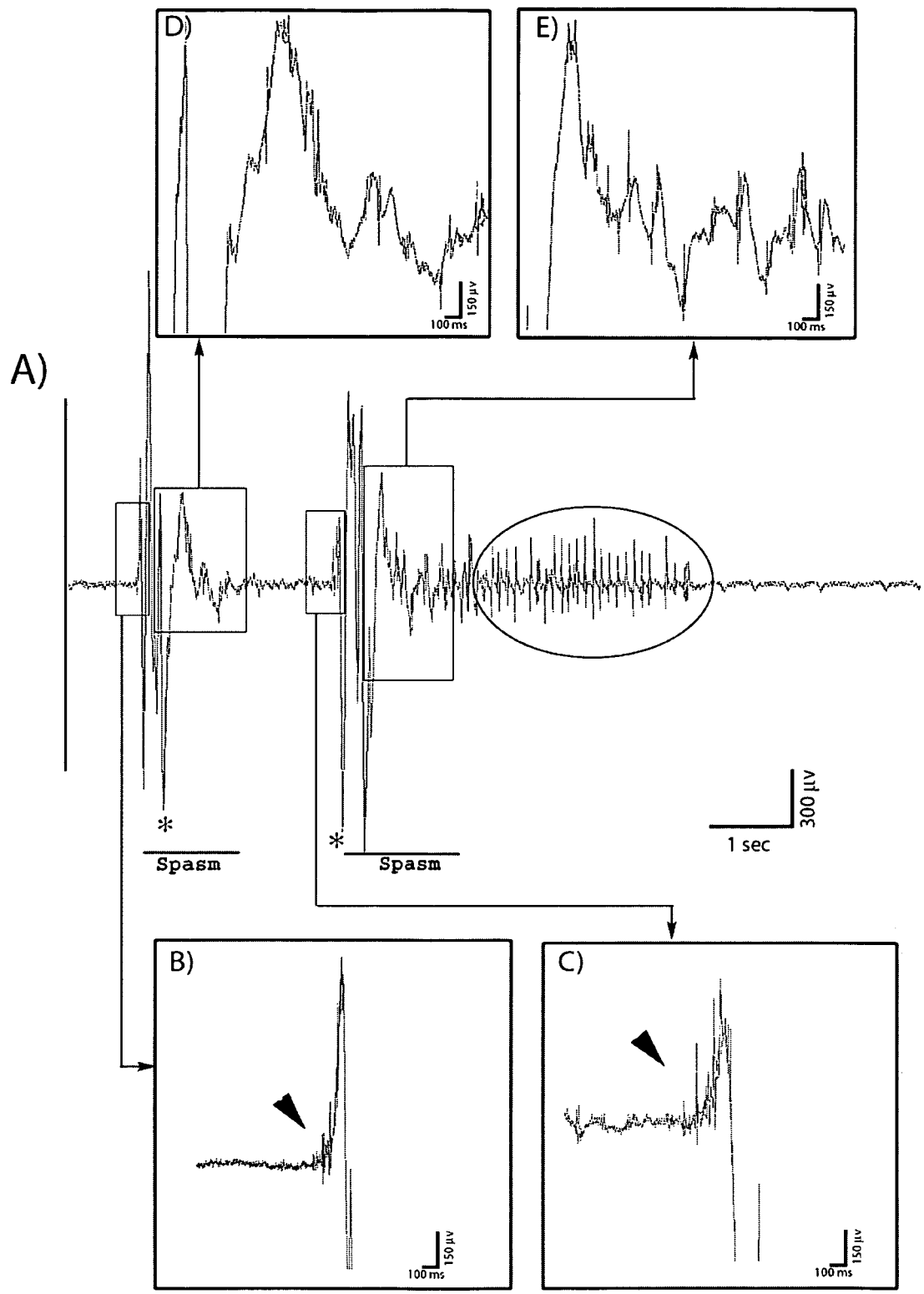
FIG. 3A-3E shows EEG patterns associated with the invention treatment. First pattern: Panel A shows an EEG obtained during a brief cluster consisting of 2 spasms in a P9 pup following injections of DOX, LPS and PCPA. This pup had 15 spasms during the 45 min that it was monitored. The ictal discharge is characterized by the initial appearance of rapid polyspike activity, which precedes the appearance of the behavioral seizure (Panels B and C, arrowheads, expanded time frame). A movement artifact obscures the onset of the spasm (asterisk). The EEG correlate during the latter part of the spasm consists of a slow wave with overriding polyspikes resembling a possible electrodecremental discharge (Panels D and E, expanded time frame). Compare with FIG. 4A which shows the ictal EEG in a human infant undergoing a spasm. The spasm is associated with a burst of fast polyspikes (left arrow) followed by an electrodecremental response (right arrow). Second pattern: Panel F shows an EEG recorded during another spasm. Note the lack of polyspike activity preceding the spasm. The arrow points to the time the polyspikes were seen in the spasms depicted in Panels B and C. The different patterns observed at the ictal onset may indicate that there are various generators of the spasms. The second spasm in Panels A-E is followed by a focal discharge (circled). This has also been described to occur in some humans with symptomatic IS. Compare with FIG. 4B, showing, in another human infant, that the spasm is also followed by a focal EEG discharge (circled).
Figure 4:
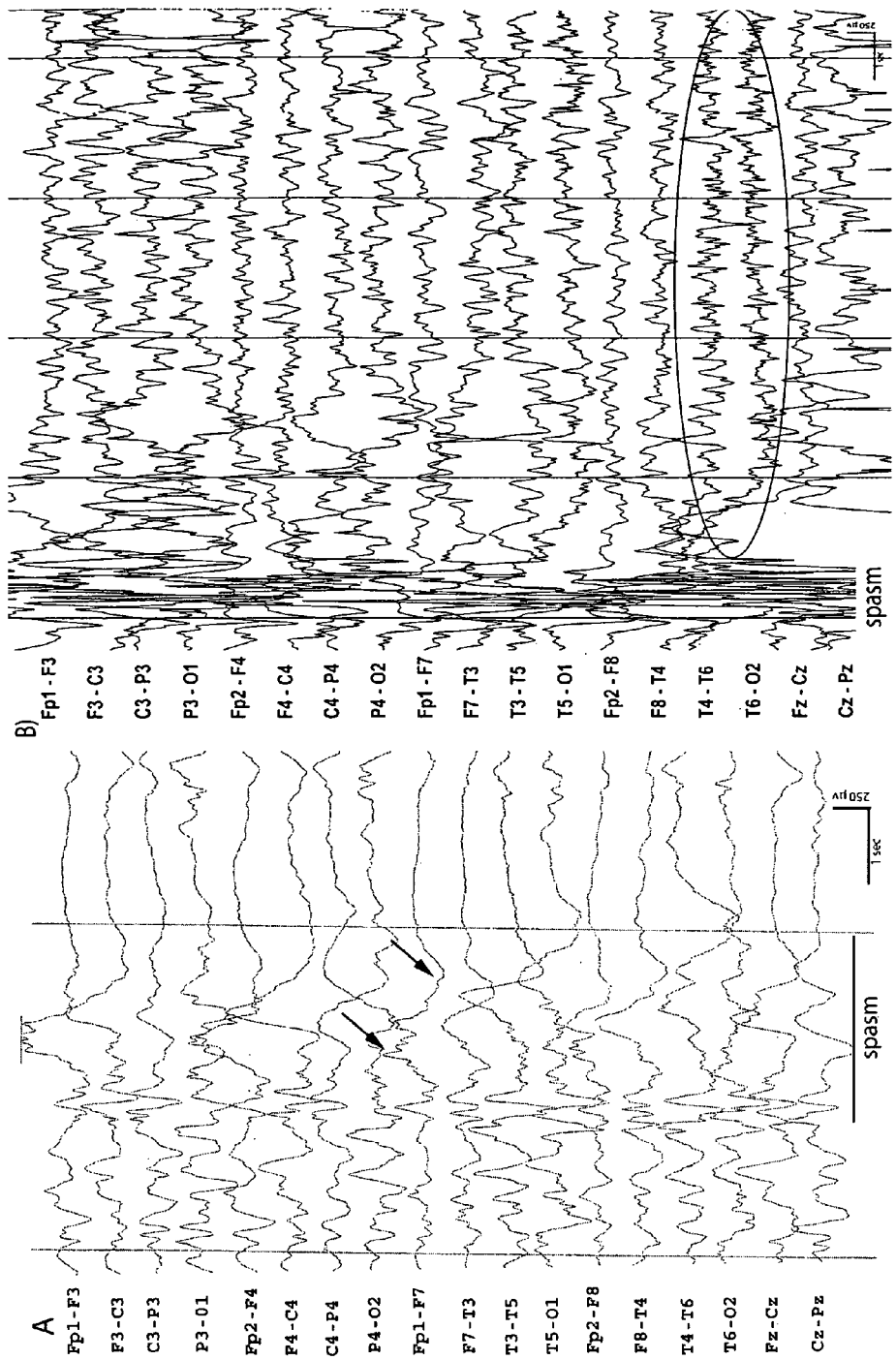
FIG. 4A-4B shows ictal EEG recordings obtained during spasms in a human baby; longitudinal bipolar montage. Panel A shows the recordings of a 5 month old infant. The EEG correlates of the spasm include a burst of polyspikes (left arrow) followed by an electrodecremental response (right arrow). Panel B shows the recordings of a 7 month old infant. Notice the focal right posterior temporal discharge following the spasm (circled).

The flexion spasms were phenotypically similar to those observed during the behavioral studies. The EEG showed ictal discharges that were time-locked with the spasms. Two patterns were observed. In the first pattern (FIG. 3A), the spasms were preceded by the onset of rapid polyspike activity (FIG. 3, inserts B and C). In the second pattern, the polyspike activity is absent suggesting that this spasm has a different generator from the spasms depicted in FIG. 3A. Inserts D and E depict possible electrodecremental responses, that in some aspects resemble the discharges seen in humans with IS (FIG. 4). Focal discharges sometimes persisted after the end of the spasm (circled).

Figure 5:
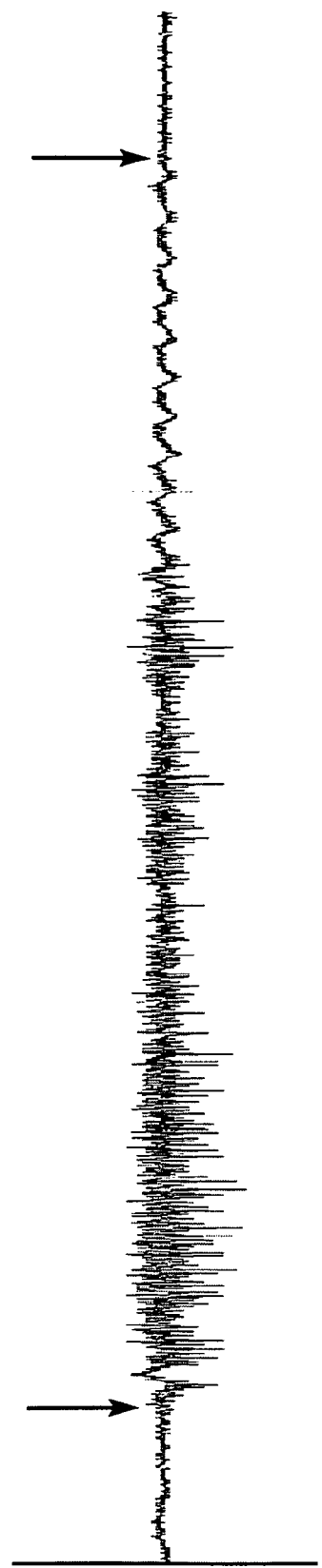
FIG. 5 shows the EEG seizure discharge recorded from the left hippocampus in a P11 pup. The arrows indicate the beginning and the end of the seizure. The seizure is characterized by the appearance of a fast polyspike discharge, waxing and waning over time followed by rhythmic slowing prior to the end of the seizure. During the seizure the rat exhibited behavioral arrest without any clonic movements. This pup had experienced recurrent spasms during the previous two days. Spasms were not observed during this monitoring session.

Limbic seizures. At P12, two pups developed behavioral evidence of bilateral clonic seizures of limbic origin (modified Racine stage 5 seizures as described by Haas et al., 1990). Another rat developed multiple episodes of behavioral arrest associated with ictal EEG discharges at P11 (FIG. 5). During this session, spasms were not observed.

Figure 6:
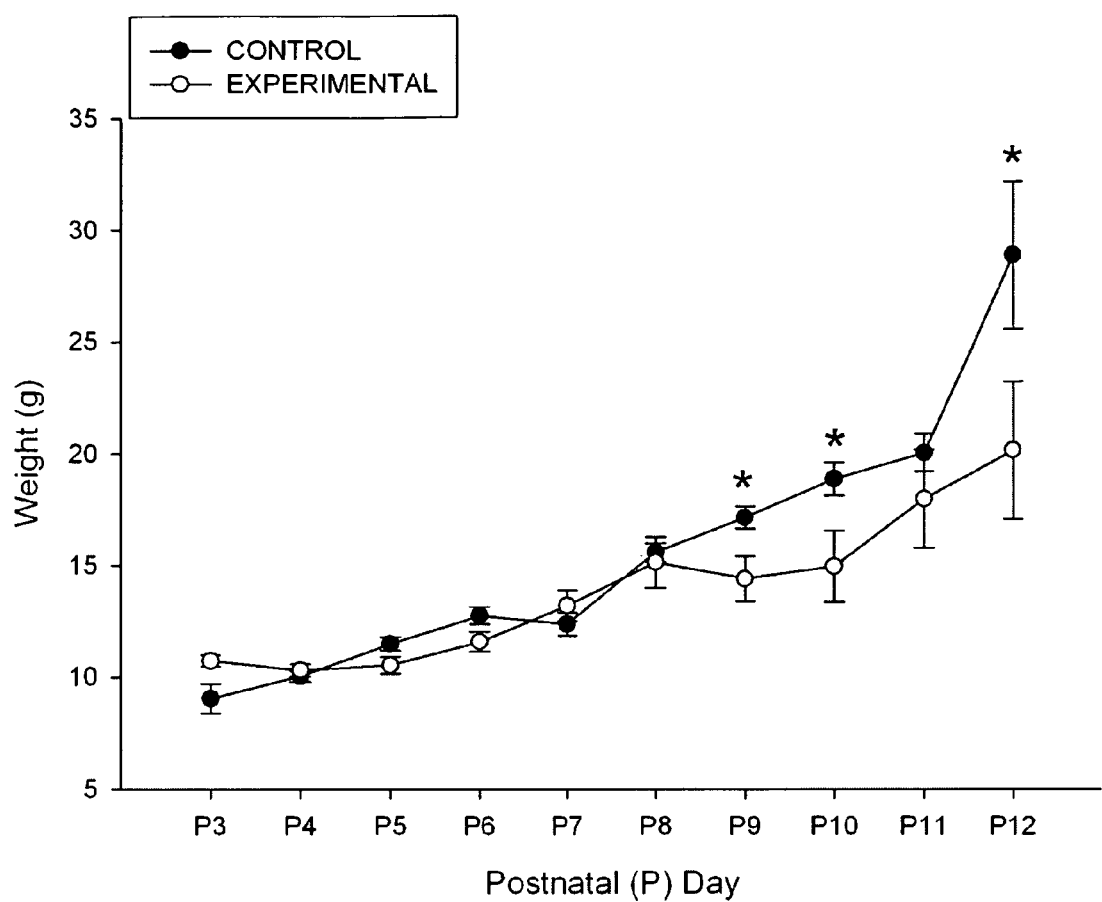
FIG. 6 is a graph showing the daily weight measurements in pups injected with DOX and LPS at P3 and PCPA at P5, compared with controls. There were no significant differences in the weights of experimental and control pups from P3-6. After P8, experimental pups gained weight at a slower rate than controls. In the experimental group, there is a transient arrest of weight gain from P8 to P10; (two way ANOVA, P<0.01; values are mean±SEM; asterisk indicates p<0.01 in all pairwise multiple comparison procedures, Holm-Sidak method).

Effects on growth. In this preliminary study, we used as controls naive non-injected rats. There were no significant differences in the weights of experimental and control pups from P3-6. After P8, experimental pups gained weight at a slower rate than controls with a transient arrest of weight gain from P8 to P10 (FIG. 6). This transient arrest in weight may be related to the effect of the drugs and possibly to the presence of recurrent spasms that may prevent the pups from successfully feeding.

Figure 7:
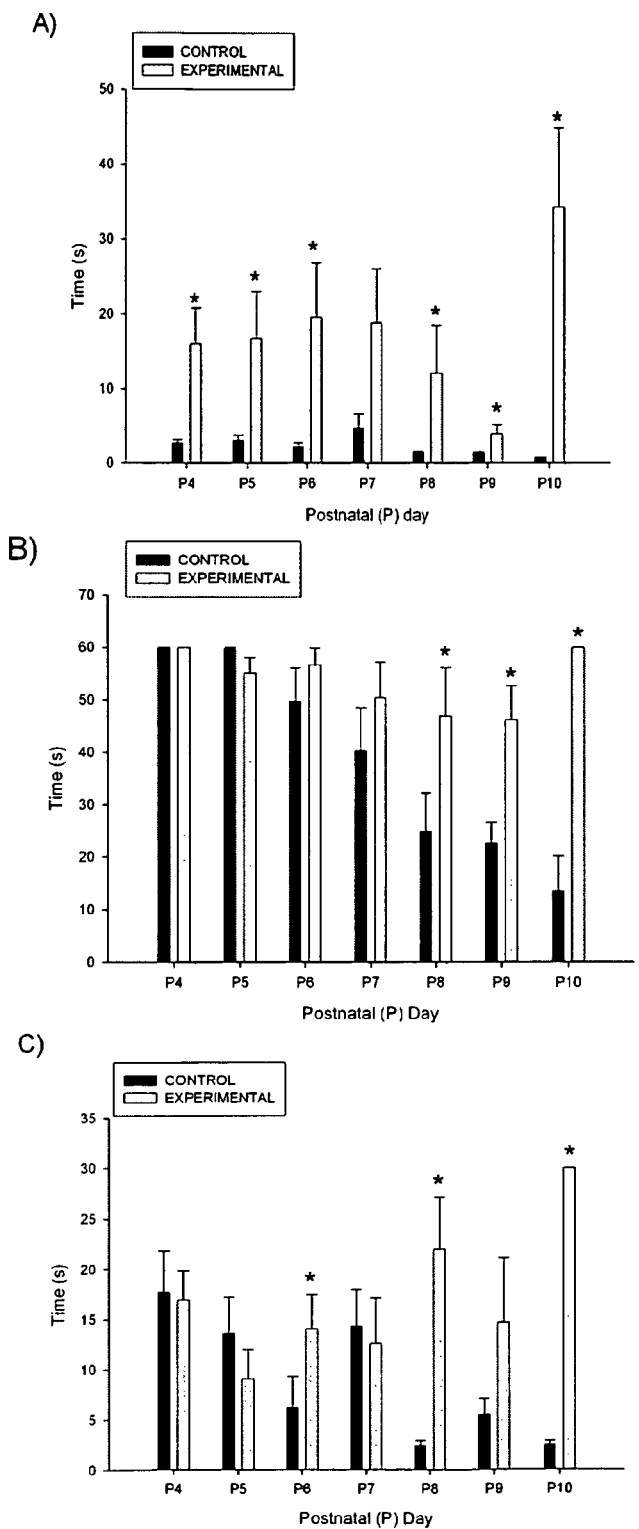
FIG. 7A-7C is graphs of results of motor development experiments with experimental and control rat pups. Panel A shows the results of surface righting experiments. Panel B shows the results of open field experiments. Panel C shows the results of negative geotaxis experiments. In all three tests, there was a significant interaction between age and prior treatment (two-way ANOVA, p<0.05). In addition, in the open field and negative geotaxis tests, the performance of controls significantly improved with age. This was not the case in experimental rats. In the open field and negative geotaxis tests, the differences between experimental and controls were more pronounced after P7 when spasms were observed (values are mean±SEM; asterisk indicates p<0.05).

Assessment of motor development. Experimental and control non-injected rat pups underwent behavioral testing to assess surface righting, open field activity and negative geotaxis (FIG. 7). Surface righting is the time taken in seconds for pups placed in the supine position to return to the prone position; open field activity assessment is a measure of exploratory behavior; negative geotaxis is the time taken for a pup placed head down on a 45° incline to turn 90° and begin crawling up the slope. Experimental pups had worse performance in all three tests attributable in part to the injury produced by the administration of DOX, LPS and PCPA. In the open field and negative geotaxis assessments, the differences between experimental and controls were more pronounced after P7 at the time of maximal expression of the spasms. These results suggest that the rats in our model fail to achieve the developmental milestones at the same rate as controls.

Mortality. Three rats died two days after the completion of the injections; spasms were not observed in these pups. Three other pups without any observed spasms died at P8 and P9. These rats were cannibalized and their brains were not available for histology. Of the seven rats with spasms, 4 survived to P12 when they were sacrificed for histology (see Pathological Findings, below). Thus, 3/7 the pups with spasms died indicating a mortality rate of 43%. It should be emphasized that mortality in children with IS is high (5-30%) (Riikonen, 1982; Snead et al., 1983; Rantala and Putkonen, 1999; Appleton, 2001; Mackay et al., 2002).

Figure 8:
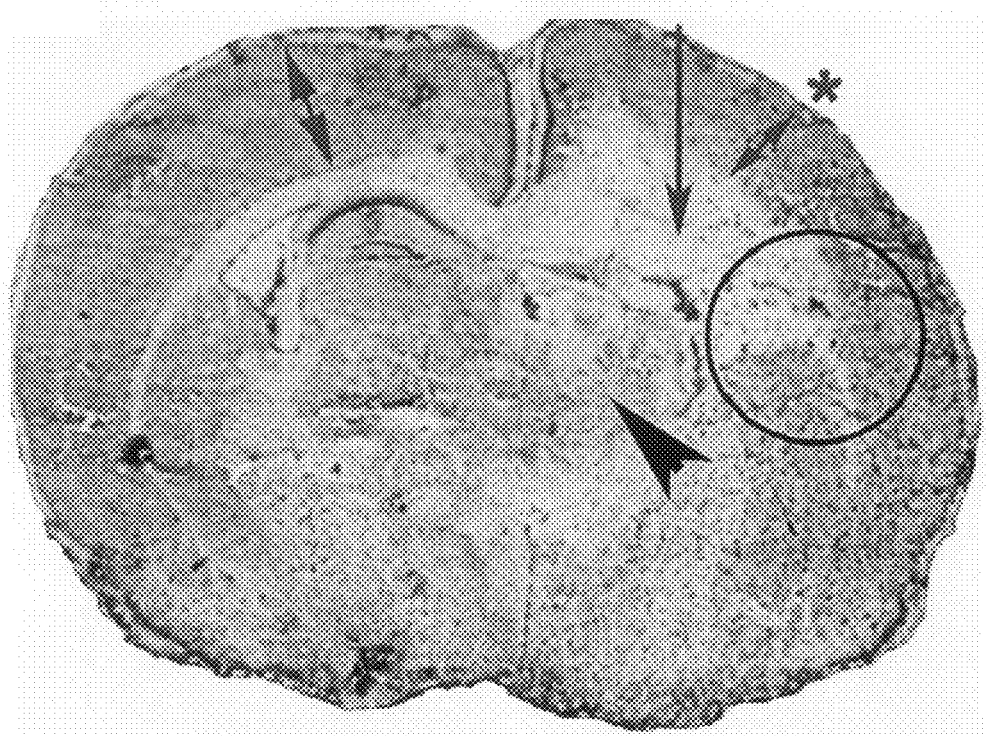
FIG. 8 shows a thionin stained coronal section of a brain obtained from a P12 pup that developed spasms and recurrent limbic seizures following the injections of DOX and LPS in the right hemisphere at P3 and PCPA i.p. at P5. There is marked hemiatrophy, ipsilaterally to the injection site. For example there is thinning of the right cortex (*, note the length of the double headed arrows on either side); the right dorsal hippocampus is destroyed (single headed arrow); there is damage to the corpus callosum fibers on the right (circle); and disorganization and shrinkage of the right thalamus.

Pathological findings. The injections result in significant injury involving several regions of the brain. FIG. 8 shows some of the characteristic findings.

Methods

Anesthesia. Rat pups were anesthetized with 2% isoflurane in 100% $O_2$ continuously delivered by a small facemask, custom-fitted to the stereotaxic frame.

Injections of DOX and LPS. Both male and female rats were used. At P3, stereotaxic injections of DOX and LPS were performed using a 25 µL Hamilton syringe. DOX was injected into the right ventricle (AP=−1.0, ML=1.1, DV=−3.3, reference to bregma) and LPS into the right cerebral hemisphere (AP=−1.0, ML=1.0, DV=2.0, reference to bregma). The injection volume is 5 µl for DOX and 7 µl for LPS. The pups were allowed to recover before returning to the dam.

Stereotaxic placement of electrodes for EEG monitoring. At P7, bilateral epidural electrodes were placed in the parietal bone, 1 mm behind and 1 mm lateral to bregma. After a period of recovery, the pups underwent intermittent CCTV-EEG monitoring until the end of the studies. Hippocampal electrodes were placed in selected rats at P11 (the age rats with spasms develop limbic seizures as shown by our preliminary results) to monitor the development of limbic seizures. The placement of the depth electrode was verified histologically using standard techniques (Haas et al., 1990). The initial coordinates were as follows: AP=−4.0, ML=−3.3, DV=−6.0 and were modified as needed.

Example 2

Dose Titration and Epidural EEG

Figure 9:
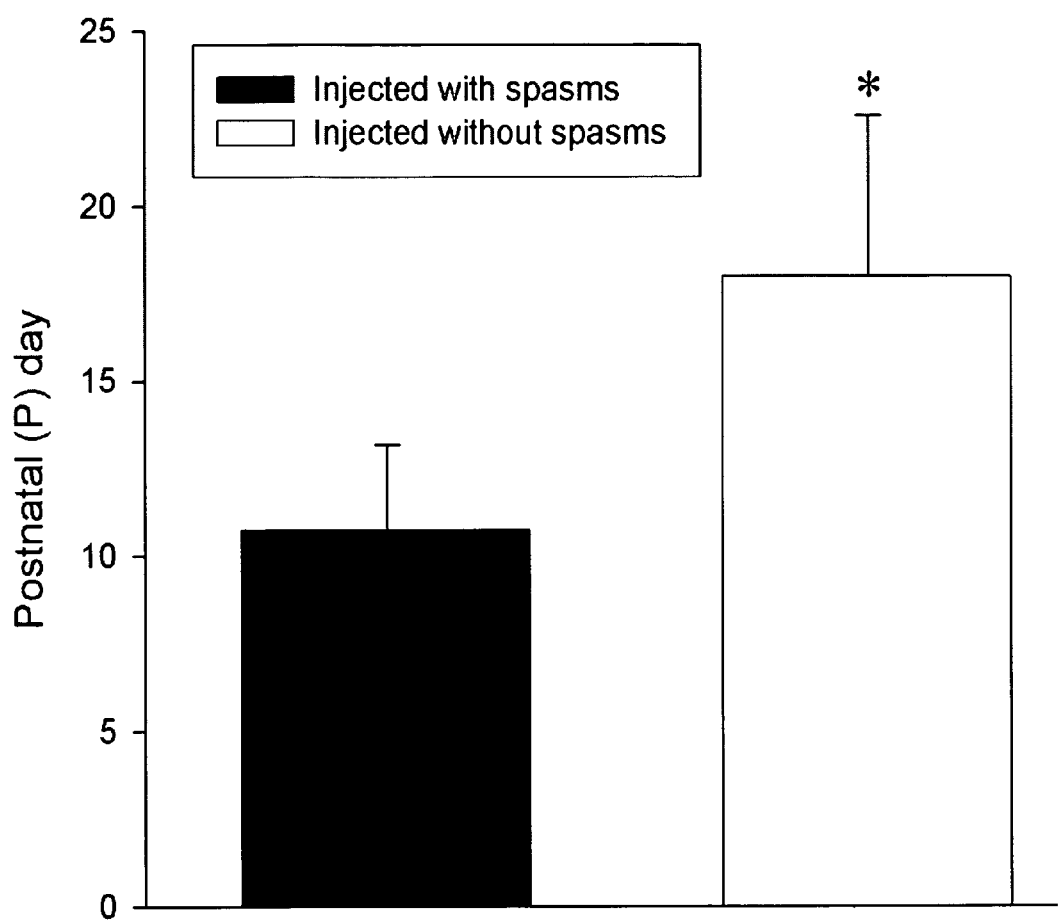
FIG. 9 is a graph showing mortality in pups injected with DOX (1 µg/g) and LPS (1 µg/g) at P3 and PCPA 150 mg/kg at P5. Pups without spasms (n=3) lived significantly longer than those having spasms (n=8; p<0.001, student-t-test). The two pups that died at P7 were excluded from the group without spasms as they were only monitored at P5 and 6 and the preliminary results suggest that spasms do not occur in pups prior to P7. The graph depicts the mean age of mortality±S.D.

Titration of doses of agents used to induce spasms. Because the time course of the spasms appears to correlate with the time course of the PCPA effect on serotonin (Rattray et al., 1996), five pups were injected with PCPA only; none of those pups developed spasms. To further identify the best combination of doses (DOX, LPS and PCPA) that would result in low mortality but permit for the maximal expression of the spasms, the volume of the intracerebral injections was initially reduced while maintaining the same concentrations: P3 pups were injected with DOX (1 µg/g, 4 µl instead of 5 µl) and LPS (1 µg/g, 3 µL instead of 7 µL). The dose of PCPA was also adjusted to 150 mg/kg i.p. (instead of 300 mg/kg) given at P5 because serotonin is known to decrease sucking in rat pups (Spear and Ristine, 1982; Ristine and Spear, 1984); this may impact survival. Spasms were observed in 8/13 (62%) of pups between the ages of P7 to P12. Four of those pups died at P9 and the others died at P10, 11, 14 and 15. Five pups (38%) did not develop spasms. Two of those pups died at P7 and the others died at P14, 17 and 23. When comparing mortality rates after P7 (the day the spasms are first observed) in pups without spasms to pups with spasms, pups without spasms lived significantly longer (FIG. 9) which indicates that, in addition to pathology and maternal factors, the spasms may have a considerable impact on the survival of the pups.

Figure 10:
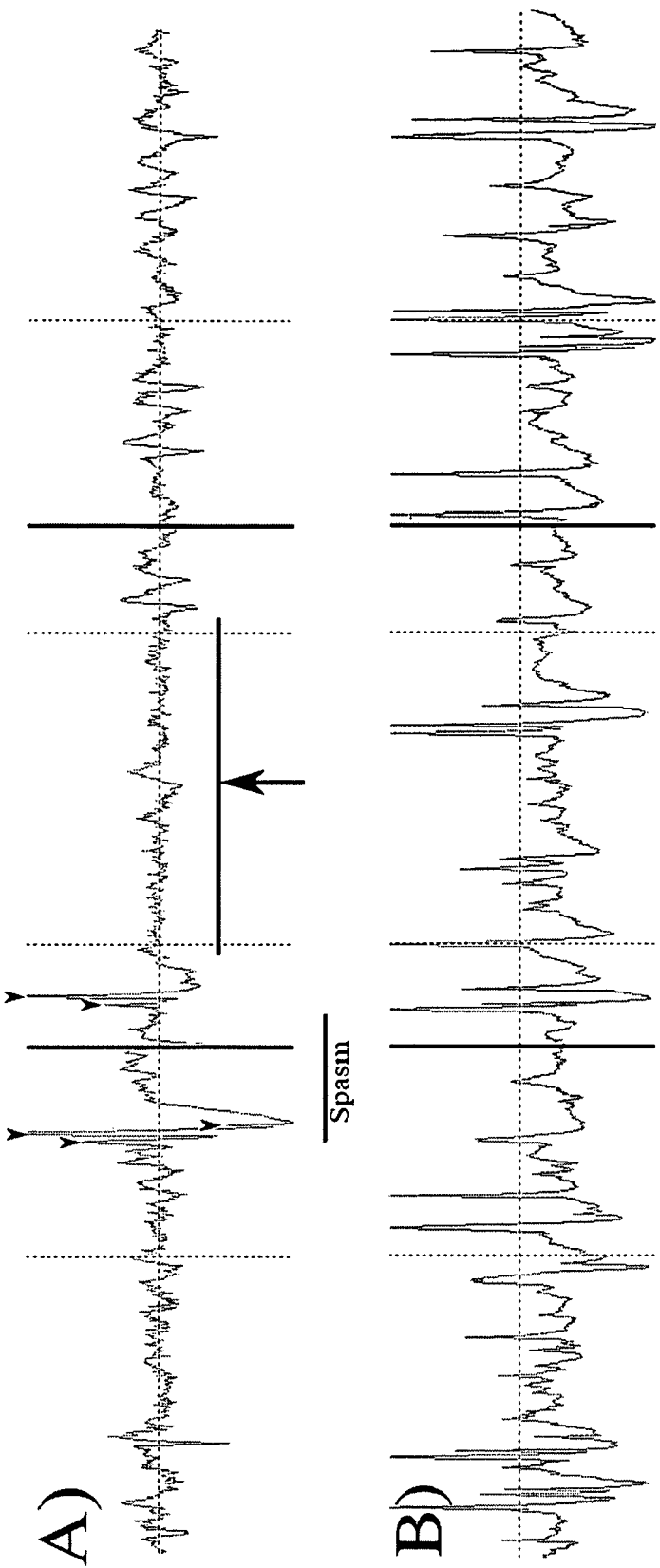
FIG. 10A-10B is EEG traces obtained in a P8 pup with epidural electrodes located in the central regions bilaterally. Panel A shows that the spasm was associated with an initial polyspike (first three arrowheads) and slow wave discharge. Immediately after the spasm there was a second run of spikes (second two arrowheads) and relative attenuation of the background activity (voltage attenuation; horizontal line with arrow). Once again these changes resemble an electrodecremental response. Panel B shows interictal EEG abnormalities recorded during this session showing high amplitude spike/polyspike and slow wave activity not associated with any behavioral manifestations. Scale: horizontal bar=1 second; vertical bar=100 µV. The thick vertical lines represent 10 second epochs.

Epidural EEG recordings. EEGs were recorded from epidural electrodes located in the parietal bone (central regions) bilaterally in three pups experiencing spasms. The electrodes were inserted at P7 in all pups. The electrodes remained in place in all the pups for the duration of the experiment (P11). In these pups the spasms were associated with a burst of high amplitude spikes or sharps wave discharges that were sometimes followed by voltage attenuation of the EEG (FIG. 10A). The interictal EEG often showed intermittent epileptic abnormalities including runs of high amplitude spike and slow wave discharges that were not associated with abnormal behaviors (FIG. 10B).

REFERENCES

Alvarez L A, Shinnar S, Moshe S L. Infantile spasms due to unilateral cerebral infarcts. Pediatrics. 1987;79:1024-1026

Appleton R E. West syndrome: long-term prognosis and social aspects. Brain Dev. 2001;23:688-691

Asano E, Chugani D C, Juhasz C et al. Surgical treatment of West syndrome. Brain Dev. 2001;23:668-676

Asano E, Juhasz C, Shah A et al. Origin and propagation of epileptic spasms delineated on electrocorticography. Epilepsia. 2005;46:1086-1097

Avanzini G, Panzica F, Franceschetti S. Brain maturational aspects relevant to pathophysiology of infantile spasms. Int Rev Neurobiol. 2002;49:353-365

Avishai-Eliner S, Brunson KL, Sandman C A, Baram T Z. Stressed-out, or in (utero)? Trends Neurosci. 2002;25:518-524

Bachman D S. Spontaneous remission of infantile spasms with hypsarhythmia. Arch Neurol. 1981;38:785

Baird H W, 3rd. Convulsions in infancy and childhood. Conn Med. 1959;23:149-151

Baram T Z, Mitchell W G, Tournay A et al. High-dose corticotropin (ACTH) versus prednisone for infantile spasms: a prospective, randomized, blinded study. Pediatrics. 1996;97:375-379

Beierle E A, Chen M K, Hartwich J E et al. Artificial rearing of mouse pups: development of a mouse pup in a cup model. Pediatr Res. 2004;56:250-255

Bertram E H, Cornett J. The ontogeny of seizures in a rat model of limbic epilepsy: evidence for a kindling process in the development of chronic spontaneous seizures. Brain Res. 1993;625:295-300

Bingham P M, Spinner N B, Sovinsky L et al. Infantile spasms associated with proximal duplication of chromosome 15q. Pediatr Neurol. 1996;15:163-165

Bobo J K, Thapa PB, Anderson J R, Gale J L. Acute encephalopathy and seizure rates in children under age two years in Oregon and Washington state. Am J Epidemiol. 1994;140:27-38

Burnham W M. Core mechanisms in generalized convulsions. Fed Proc. 1985;44:2442-2445

Brunson K L, Eghbal-Ahmadi M, Baram T Z. How do the many etiologies of West syndrome lead to excitability and seizures? The corticotropin releasing hormone excess hypothesis. Brain Dev. 2001a;23:533-538

Brunson K L, Khan N, Eghbal-Ahmadi M, Baram T Z. Corticotropin (ACTH) acts directly on amygdala neurons to down-regulate corticotropin-releasing hormone gene expression. Ann Neurol. 2001b;49:304-312

Caplan R, Siddarth P, Mathern G et al. Developmental outcome with and without successful intervention. Int Rev Neurobiol. 2002;49:269-284

Caraballo R, Cersosimo R, Intruvini S et al. [West's syndrome in patients with cerebral paralysis and periventricular leukomalacia: a good response to treatment]. Rev Neurol. 1997;25:1362-1364

Caraballo R H, Fejerman N, Bernardina B D et al. Epileptic spasms in clusters without hypsarrhythmia in infancy. Epileptic Disord. 2003;5:109-113

Carmant L, Goodyear E, Sauerwein C. The use of calcium channel blockers in the treatment of West syndrome. Neurology. 2000;54:A295

Chugani H T, Shewmon D A, Sankar R et al. Infantile spasms: II. Lenticular nuclei and brain stem activation on positron emission tomography. Ann Neurol. 1992;31:212-219

Curatolo P. Infantile spasms (West's syndrome). In: Maria B L, ed. Current management of child neurology. 3 ed. Hamilton, Ontario: B C Decker, 2005:134-138

Cusmai R, Ricci S, Pinard J M et al. West syndrome due to perinatal insults. Epilepsia. 1993;34:738-742

Dalla Bernardina B, Fontana E, Vigevano F et al. Efficacy and tolerability of vigabatrin in children with refractory partial seizures: a single-blind dose-increasing study. Epilepsia. 1995;36:687-691

Djukic A, Lado F A, Shinnar S, Moshe S L. Are early myoclonic encephalopathy (EME) and the Ohtahara syndrome (EIEE) independent of each other. Epilepsy Res. 2006; In press Druckman R, Chao D. Massive spasms in infancy and childhood. Epilepsia. 1955;4:61-72

Dulac O, Feingold J, Plouin P et al. Genetic predisposition to West syndrome. Epilepsia. 1993a;34:732-737

Dulac O, Plouin P, Jambaque I. Predicting favorable outcome in idiopathic West syndrome. Epilepsia. 1993b;34:747-756

Dulac O, Plouin P, Schlumberger E. Infantile spasms. In: Wyllie E, ed. The treatment of epilepsy: principals and practice. 2 ed. Baltimore, Md.: Williams & Wilkins, 1997:540-572

Favata I, Leuzzi V, Curatolo P. Mental outcome in West syndrome: prognostic value of some clinical factors. J Ment Defic Res. 1987;31 (Pt 1):9-15

Gibbs F A, Gibbs E L. Atlas of electroencephalography. 2 vol. Cambridge, Mass.: Addison-Wesley, 1952

Glauser T A, Clark P O, Strawsburg R. A pilot study of topiramate in the treatment of infantile spasms. Epilepsia. 1998;39:1324-1328

Grabenstatter H L, Ferraro D J, Williams P A et al. Use of chronic epilepsy models in antiepileptic drug discovery: the effect of topiramate on spontaneous motor seizures in rats with kainate-induced epilepsy. Epilepsia. 2005;46:8-14.

Haas K, Sperber E F, Moshé S L. Kindling in developing animals: expression of severe seizures and enhanced development of bilateral foci. Developmental Brain Research. 1990;56:275-280

Haines S T, Casto D T. Treatment of infantile spasms. Ann Pharmacother. 1994;28:779-791

Hashimoto K, Enokido H, Koizumi Y et al. MRI and autopsy findings of hypomelanosis of Ito with intractable epileptic seizures: report of two cases. Jpn J Psychiatry Neurol. 1990;44:414-416

Hayashi M, Itoh M, Araki S et al. Immunohistochemical analysis of brainstem lesions in infantile spasms. Neuropathology. 2000;20:297-303

Higuchi Y, Maihara T, Hattori H et al. [18F]-fluorodeoxyglucose-positron emission tomography findings in infants with severe periventricular leukomalacia and hypsarrhythmia. Eur J Pediatr. 1997;156:236-238

Hobson J A, McCarley R W, Pivik R T, Freedman R. Selective firing by cat pontine brain stem neurons in desynchronized sleep. J Neurophysiol. 1974;37:497-511

Hrachovy R A, Frost J D, Jr. Infantile epileptic encephalopathy with hypsarrhythmia (infantile spasms/West syndrome). J Clin Neurophysiol. 2003;20:408-425

Hrachovy R A, Glaze DG, Frost J D, Jr. A retrospective study of spontaneous remission and long-term outcome in patients with infantile spasms. Epilepsia. 1991;32:212-214

Hurst D L, Rolan T D The use of felbamate to treat infantile spasms. J Child Neurol 1995 10:134-6

Jeavons P M, Bower B D. The natural history of infantile spasms. Arch Dis Child. 1961;36:17-22

Jeavons P M, Bower B D, Dimitrakoudi M. Long-term prognosis of 150 cases of "West syndrome". Epilepsia. 1973;14:153-164

Juhasz C, Chugani H T, Muzik O, Chugani D C. Hypotheses from functional neuroimaging studies. Int Rev Neurobiol. 2002;49:37-55

Kabova R, Liptakova S, Slamberova R et al. Age-specific N-methyl-D-aspartate-induced seizures: perspectives for the West syndrome model. Epilepsia. 1999;40:1357-1369

Kagawa K, Chugani D C, Asano E et al. Epilepsy surgery outcome in children with tuberous sclerosis complex evaluated with alpha-[11C]methyl-L-tryptophan positron emission tomography (PET). J Child Neurol. 2005;20:429-438

Kasai K, Watanabe K, Negoro T et al. Delayed myelination in West syndrome. Psychiatry Clin Neurosci. 1995;49:S265-266

Kellaway P, Hrachovy R A, Frost J D, Jr., Zion T. Precise characterization and quantification of infantile spasms. Ann Neurol. 1979;6:214-218

Khan O H, Enno T L, Del Bigio M R. Brain damage in neonatal rats following kaolin induction of hydrocephalus. Exp Neurol. 2006

King D W, Dyken P R, Spinks I L, Jr., Murvin A J. Infantile spasms: ictal phenomena. Pediatr Neurol. 1985;1:213-218

Koo B, Hwang P A, Logan W J. Infantile spasms: outcome and prognostic factors of cryptogenic and symptomatic groups. Neurology. 1993;43:2322-2327

Kurokawa T, Goya N, Fukuyama Y et al. West syndrome and Lennox-Gastaut syndrome: a survey of natural history. Pediatrics. 1980;65:81-88

Lado F A, Moshe S L. Role of subcortical structures in the pathogenesis of infantile spasms: what are possible subcortical mediators? Int Rev Neurobiol. 2002;49:115-140

Lawlor K M, Devlin A M. Levetiracetam in the treatment of infantile spasms. Eur J Paediatr Neurol. 2005;9:19-22

Lee C, Frost J D, Jr., Swann J W, Hrachovy RA. Neonatal blockade of cortical or hippocampal activity: A possible model of infantile spasms. AES society abtract. 2006; 3.057

Lombroso C T. A prospective study of infantile spasms: clinical and therapeutic correlations. Epilepsia. 1983; 24:135-158

Lux A L, Edwards S W, Hancock E et al. The United Kingdom Infantile Spasms Study (UKISS) comparing hormone treatment with vigabatrin on developmental and epilepsy outcomes to age 14 months: a multicentre randomised trial. Lancet Neurol. 2005;4:712-717

Mackay M, Weiss S, Snead O C, 3rd. Treatment of infantile spasms: an evidence-based approach. Int Rev Neurobiol. 2002;49:157-184

Mackay M T, Weiss S K, Adams-Webber T et al. Practise parameter: Medical treatment of infantile spasms. Neurology. 2004;62:1668-1681

Maheshwari M C, Jeavons P M. The prognostic implications of suppression-burst activity in the EEG in infancy. Epilepsia. 1975;16:127-131

McNamara J O. Kindling: an animal model of complex partial epilepsy. Ann Neurol. 1984;16 Suppl:S72-76

Mikulecka A, Mares P. NMDA receptor antagonists impair motor performance in immature rats. Psychopharmacology (Berl). 2002;162:364-372

Mizukawa M, Ohtsuka Y, Murashima I et al. West syndrome associated with chromosome abnormalities: clinicoelectrical study. Jpn J Psychiatry Neurol. 1992; 46:435-436

Morimatsu Y, Murofushi K, Handa T et al. [Pathology in severe physical and mental disabilities in children—with special reference to 4 cases of nodding spasm]. Shinkei Kenkyu No Shimpo. 1972;16:465-470

Natsume J, Watanabe K, Maeda N et al. Cortical hypometabolism and delayed myelination in West syndrome. Epilepsia. 1996;37:1180-1184

Nordli D R, Jr. Infantile seizures and epilepsy syndromes. Epilepsia. 2002;43 Suppl 3:11-16

Okumura A, Hayakawa F, Kuno K, Watanabe K. Periventricular leukomalacia and West syndrome. Dev Med Child Neurol. 1996;38:13-18

Pang Y, Cai Z, Rhodes P G. Disturbance of oligodendrocyte development, hypomyelination and white matter injury in the neonatal rat brain after intracerebral injection of lipopolysaccharide. Brain Res Dev Brain Res. 2003;140:205-214

Plouin P, Dulac O, Jalin C, Chiron C. Twenty-four-hour ambulatory EEG monitoring in infantile spasms. Epilepsia. 1993;34:686-691

Poggi S H, Park J, Toso L et al. No phenotype associated with established lipopolysaccharide model for cerebral palsy. Am J Obstet Gynecol. 2005;192:727-733

Pollack M A, Zion T E, Kellaway P. Long-term prognosis of patients with infantile spasms following ACTH therapy. Epilepsia. 1979;20:255-260

Pranzatelli M R. Infantile spasms versus myoclonus: is there a connection? Int Rev Neurobiol. 2002;49:285-314

Racine R J, Burnham W M, Gartner J G, Levitan D. Rates of motor seizure development in rats subjected to electrical brain stimulation: strain and inter-stimulation interval effects. Electroencephalogr Clin Neurophysiol. 1973;35:553-556

Rantala H, Putkonen T. Occurrence, outcome, and prognostic factors of infantile spasms and Lennox-Gastaut syndrome. Epilepsia. 1999;40:286-289

Rattray M, Baldessari S, Gobbi M et al. p-Chlorphenylalanine changes serotonin transporter mRNA levels and expression of the gene product. J Neurochem. 1996;67: 463-472

Reddy D S. Newer GABAergic agents for pharmacotherapy of infantile spasms. Drugs Today (Barc). 2002; 38:657-675

Rho J M. Basic science behind the catastrophic epilepsies. Epilepsia. 2004;45 Suppl 5:5-11

Riikonen R. A long-term follow-up study of 214 children with the syndrome of infantile spasms. Neuropediatrics. 1982;13:14-23

Riikonen R, Amnell G. Psychiatric disorders in children with earlier infantile spasms. Dev Med Child Neurol. 1981;23:747-760

Ristine L A, Spear L P. Effects of serotonergic and cholinergic antagonists on suckling behavior of neonatal, infant, and weanling rat pups. Behav Neural Biol. 1984; 41:99-126

Saltik S, Kocer N, Dervent A. Magnetic resonance imaging findings in infantile spasms: etiologic and pathophysiologic aspects. J Child Neurol. 2003;18:241-246

Satoh J, Takeshige H, Hara H, Fukuyama Y. Brain shrinkage and subdural effusion associated with ACTH administration. Brain Dev. 1982;4:13-20

Satoh J, Mizutani T, Morimatsu Y. Neuropathology of the brainstem in age-dependent epileptic encephalopathy—especially of cases with infantile spasms. Brain Dev. 1986;8:443-449

Schachter S C. Pharmacology and clinical experience with tiagabine. Expert Opin Pharmacother. 2001;2:179-187

Schwarcz R, Speciale C, Okuno E et al. Quinolinic acid: a pathogen in seizure disorders? Adv Exp Med Biol. 1986; 203:697-707

Short M P, Richardson E P, Jr., Haines J L, Kwiatkowski D J. Clinical, neuropathological and genetic aspects of the tuberous sclerosis complex. Brain Pathol. 1995;5:173-179

Siegal T, Melamed E, Sandbank U, Catane R. Early and delayed neurotoxicity of mitoxantrone and doxorubicin following subarachnoid injection. J Neurooncol. 1988; 6:135-140

Silverstein F, Johnston M V. Cerebrospinal fluid monoamine metabolites in patients with infantile spasms. Neurology. 1984;34:102-105

Snead O C, 3rd, Benton J W, Myers G J. ACTH and prednisone in childhood seizure disorders. Neurology. 1983; 33:966-970

Spear L P, Ristine L A. Suckling behavior in neonatal rats: psychopharmacological investigations. J Comp Physiol Psychol. 1982;96:244-255

Stafstrom C E, Sasaki-Adams D M. NMDA-induced seizures in developing rats cause long-term learning impairment and increased seizure susceptibility. Epilepsy Res. 2003;53:129-137

Stafstrom C E, Moshe S L, Swann J W et al. Models of pediatric epilepsies: Strategies and opportunities a workshop summary. Epilepsia. 2006; 47:1407-1414

Suzuki Y. Zonisamide in West syndrome. Brain Dev. 2001; 23:658-661 van Engelen B G, Renier W O, Weemaes C M et al. High-dose intravenous immunoglobulin treatment in cryptogenic West and Lennox-Gastaut syndrome; an add-on study. Eur J Pediatr. 1994;153:762-769

Veggiotti P, Cieuta C, Rex E, Dulac O. Lamotrigine in infantile spasms. Lancet 1994;344:1375-6

Velisek L, Moshe S L. Effects of brief seizures during development. Prog Brain Res. 2002;135:355-364

Velisek L, Kamran J, Asche S, Veliskova J. Model of infantile spasms induced by NMDA in prenatally impaired brain. Ann Neurol. 2007; In Press Veliskova J. Behavioral characterization of seizures in rats. In: Pitkanen A, Schwartzkroin P A, Moshe S L, eds. Models of seizures and epilepsy. Burlington, M A: Elsevier, 2006:601-611

Velisková J, Moshé S L. Sexual dimorphism and developmental regulation of substantia nigra function. Ann Neurol. 2001;50:596-601

Vigevano F, Cilio M R. Vigabatrin versus ACTH as first-line treatment for infantile spasms: a randomized, prospective study. Epilepsia. 1997;38:1270-1274

Watanabe K. West syndrome: etiological and prognostic aspects. Brain Dev. 1998;20:1-8

Watanabe K, Haga T, Negoro T et al. Focal spasms in clusters, focal delayed myelination, and hypsarrhythmia: unusual variant of West syndrome. Pediatr Neurol. 1994;11:47-49

Webb D W, Fryer A E, Osborne J P. Morbidity associated with tuberous sclerosis: a population study. Dev Med Child Neurol. 1996;38:146-155

West W J. On a peculiar form of infantile convulsions. Lancet. 1841;1:724-725

Wolf P S, Moshe S L. Treatment of infantile spasms. In: Johnson R T, Griffin J W, McArthur J C, eds. Current therapy in neurological disease. St. Louis, Mo.: Mosby, 2002:30-34

Yamamoto H, Murakami H, Horiguchi K, Egawa B. Studies on cerebrospinal fluid kynurenic acid concentrations in epileptic children. Brain Dev. 1995;17:327-329

Zhongshu Z, Weiming Y, Yukio F et al. Clinical analysis of West syndrome associated with phenylketonuria. Brain Dev. 2001;23:552-557

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A rat model of infantile spasms, wherein the rat is administered (i) doxorubicin intracerebrally at day 2, 3 or 4 after birth, (ii) lipopolysaccharide (LPS) intracerebrally at day 2, 3 or 4 after birth, and (iii) p-chlorophenylalanine (PCPA) systemically at day 4, 5 or 6 after birth, wherein the rat exhibits recurrent flexion or extension spasm seizures, and wherein the rat exhibits rapid polyspike activity preceding the seizure on an ictal EEG.

2. The model of claim 1, wherein the rat is administered (i) doxorubicin intracerebrally at day 3 after birth, (ii) lipopolysaccharide (LPS) intracerebrally at day 3 after birth, and (iii) p-chlorophenylalanine (PCPA) systemically at day 5 after birth.

3. The model of claim 1, wherein the rat is administered 0.1-5 µg/g doxorubicin, 0.1-5 µg/g, and 30-1000 mg/kg PCPA.

4. The model of claim 1, wherein the rat is administered 0.5-2 µg/g doxorubicin, 0.5-2 µg/g LPS, and 100-600 mg/kg PCPA.

5. The model of claim 1, wherein the rat is administered about 1 µg/g doxorubicin, about 1 µg/g LPS, and about 300 mg/kg PCPA.

6. The model of claim 1, wherein the rat exhibits a recurrent flexion seizure.

7. The model of claim 1, wherein the rat exhibits an extension spasm seizure.

8. The model of claim 1, wherein rat further exhibits a deficiency in motor development.

9. The model of claim 8, wherein the deficiency in motor development is in surface righting, negative geotaxis, cliff aversion, open field activity, rooting, forelimb placing, air righting, eye-opening, horizontal bar, rotarod or a Morris water-maze test.

10. The model of claim 8, wherein the deficiency in motor development is in surface righting, negative geotaxis or open field activity.

11. A method of making a rat model of infantile spasms, the method comprising administering to the rat (i) doxorubicin intracerebrally at day 2, 3 or 4 after birth, (ii) lipopolysaccharide (LPS) intracerebrally at day 2, 3 or 4 after birth, and (iii) p-chlorophenylalanine (PCPA) systemically at day 4, 5 or 6 after birth, wherein the rat exhibits recurrent flexion or extension spasm seizures, and wherein the rat exhibits rapid polyspike activity preceding the seizure on an ictal EEG.

12. The method of claim 11, wherein the rat is administered (i) doxorubicin intracerebrally at day 3 after birth, (ii) lipopolysaccharide (LPS) intracerebrally at day 3 after birth, and (iii) p-chlorophenylalanine (PCPA) systemically at day 5 after birth.

13. The method of claim 11, wherein the rat is administered 0.1-5 µg/g doxorubicin, 0.1-5 µg/g, and 30-1000 mg/kg PCPA.

14. The method of claim 11, wherein the rat is administered 0.5-2 µg/g doxorubicin, 0.5-2 µg/g LPS, and 100-600 mg/kg PCPA.

15. The method of claim 11, wherein the rat is administered about 1 µg/g doxorubicin, about 1 µg/g LPS, and about 300 mg/kg PCPA.

16. The method of claim 11, wherein the rat exhibits a recurrent flexion seizure.

17. The method of claim 11, wherein the rat exhibits an extension spasm seizure.

18. The method of claim 11, wherein rat further exhibits a deficiency in motor development.

19. The method of claim 18, wherein the deficiency in motor development is in surface righting, negative geotaxis, cliff aversion, open field activity, rooting, forelimb placing, air righting, eye-opening, horizontal bar, rotarod or a Morris water-maze test.

20. The method of claim 18, wherein the deficiency in motor development is in surface righting, negative geotaxis or open field activity.

21. A method of screening a compound for the potential to attenuate a symptom of infantile spasms, the method comprising administering the compound to the rat of claim 1, and determining whether the compound attenuates a symptom characteristic of infantile spasms in the rat.

* * * * *